US00PP28505P3

(12) United States Plant Patent
Bradford et al.

(10) Patent No.: US PP28,505 P3
(45) Date of Patent: Oct. 10, 2017

(54) PEACH TREE NAMED 'PEARL PRINCESS III'

(50) Latin Name: *Prunus persica*
Varietal Denomination: Pearl Princes III

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 38 days.

(21) Appl. No.: 14/757,251

(22) Filed: Dec. 11, 2015

(65) Prior Publication Data

US 2017/0172031 P1 Jun. 15, 2017

(51) Int. Cl.
*A01H 5/08* (2006.01)

(52) U.S. Cl.
USPC ..... Plt./195

(58) Field of Classification Search
USPC ..... Plt./195
See application file for complete search history.

(56) References Cited

U.S. PATENT DOCUMENTS

PP13,496 P2 1/2003 Bradford
PP19,919 P2 4/2009 Bradford

*Primary Examiner* — Keith Robinson

(57) ABSTRACT

The present invention relates to a new and distinct variety of peach tree, *Prunus persica*, broadly characterized by a small to medium size, moderately weak, hardy, self-fertile, productive and regular bearing tree. The variety blooms during the early season and requires about 350 chilling hours. The fruit matures under the ecological conditions described in early June, with first picking on Jun. 3, 2015. The fruit is uniform, large in size, globose in shape, clingstone in type, firm and melting in texture, mostly red in skin color, white in flesh color, and sub-acid in flavor.

1 Drawing Sheet

Botanical classification: *Prunus persica.*
Variety denomination: 'PEARL PRINCESS III'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'Pearl Princess III'.

The present variety was hybridized by us in 2008 as a first generation cross using 'Pearl Princess V' (U.S. Plant Pat. No. 19,919) peach as the selected seed parent and '0P9' yellow flesh peach (unpatented) as the selected pollen parent. Upon reaching maturity the fruit of this cross was gathered, and the seeds were removed, cracked, stratified, germinated, and grown as seedlings on their own root in our greenhouse. Upon reaching dormancy the seedlings were transplanted as a group to a cultivated area of our experimental orchard located near Le Grand, Calif., in Merced County (San Joaquin Valley). During the fruit evaluation season of 2012 we selected the present variety as a single tree from the group of seedlings described above. Subsequent to origination of the present variety of peach tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its pollen parent, '0P9' peach (unpatented), by being self-fertile and by producing fruit that is large in size, mostly red in skin color, and globose in shape, but is quite distinguished therefrom by producing fruit that is white instead of yellow in flesh color, that is firmer in texture, and that ripens about forty-five days later.

The present variety is most similar to its seed parent, 'Pearl Princess V' (U.S. Plant Pat. No. 19,919) peach, by having showy blossoms, by having reniform leaf glands, by being self-fertile, and by producing white flesh peaches that are mostly red in skin color, nearly globose in shape, and firm in texture, but is distinguished therefrom by having a smaller and less vigorous tree, by blooming earlier, by requiring less chilling hours, and by producing fruit that is clingstone instead of freestone in type, that is somewhat lower in acid, and that matures about seven days earlier.

The present variety is also similar to 'Ivory Queen' peach tree (U.S. Plant Pat. No. 13,496), by having a medium size tree, by having showy blossoms, by having reniform leaf glands, by being self-fertile, and by producing white flesh peaches that are clingstone in type, mostly red in skin color, nearly globose in shape, firm in texture, and sub-acid in flavor, but is distinguished therefrom by blooming much earlier, by requiring less chilling hours, and by producing fruit that is much larger in size and that matures about five days earlier.

SUMMARY OF VARIETY

In summary, the present peach variety is characterized by a small to medium size, moderately weak, hardy, self-fertile, productive and regular bearing tree. The variety blooms during the early season and requires about 350 chilling hours. The fruit matures under the ecological conditions described in early June, with first picking on Jun. 3, 2015. The fruit is uniform, large in size, globose in shape, clingstone in type, firm and melting in texture, mostly red in skin color, white in flesh color, and sub-acid in flavor.

DRAWING

The accompanying photograph consists of four whole fruits positioned to display the characteristics of the skin color and form, a half fruit to reveal the flesh, an individual stone, typical leaves, a typical tip shoot, and two insets depicting a flower bud and blossom as they appeared on the tree during the blooming season.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of shipping ripe on Jun. 5, 2015, on the original tree during its seventh growing season. The blossom and flower descriptions were made the previous blooming season. All major color code designations are by reference to the Inter-Society Color Council, National Bureau of Standards. Common color names are also used occasionally.

It is to be noted that the 2015 fruit season in California was very warm during the spring and the ripening times of almost all varieties were about twenty days earlier than other years.

PARENTAGE

Seed parent: 'Pearl Princess V' (U.S. Plant Pat. No. 19,919) peach.

Pollen parent: '0P9' (unpatented) peach.

TREE

Size: Small to medium, reaching and maintaining a height of 8' [2.44 m.] and a spread of 4' [1.22 m.] after seven growing seasons utilizing typical dormant pruning.

Vigor: Moderately weak, responding below average to irrigation and fertilization. The variety grows about 2' [0.91 m.] of surplus top-growth during the spring and summer. The plant should be grown on a standard commercial rootstock for production purposes.

Growth: Spreading and dense.

Form: Pruned to a Perpendicular V type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 350 hours.

Trunk:

*Size.*—Medium to slender, reaching a maximum diameter of 3¾" [95 mm.] after the seventh growing season.

*Texture.*—Medium roughness.

*Bark color.*—A Moderate brown [58. m.Br] and Grayish brown [61. gy.Br] variegation.

*Lenticels.*—Approximate Number Per Square Inch: 5. Color: Brownish orange [54. brO]. Average Size: ¼" [6.4 mm.] in length. The width is typically one fourth as much as the length. Shape: Eye-shaped.

Branches:

*Size.*—Medium to slender, diameter of main scaffold is 2" [51 mm.] measured 12" above the crotch, diameter of first side hanger is ¾" [19 mm.] measured 6" from the main scaffold.

*Texture.*—Fairly smooth on first and second year wood, increasing roughness with age.

*Color.*—1st Year Wood Topside: Moderate red [15. m.R]. 1st Year Wood Underside: Brilliant yellow green [116. brill.YG]. 2nd Year and Older Wood: Light brownish gray [63. l.brGy] to Dark brown [59. d.Br].

*Lenticels.*—Number Per Square Inch: About 50 on second year wood. Color: Light yellowish brown [76. l.yBr]. Average Size: Small, 1/64" [0.4 mm.] in length. The width is typically one fourth as much as the length. Shape: Eye-shaped.

Leaves:

*Size.*—Medium. Average Length: 5¼" [133.4 mm.]. Average Width: 1½" [38.1 mm.].

*Arrangement.*—Alternate.

*Thickness.*—Medium.

*Form.*—Elliptical.

*Apex.*—Acuminate.

*Base.*—Mostly acute with an average base angle of 70 degrees.

*Surface.*—Smooth on both sides.

*Color.*—Dorsal Surface: Moderate olive green [125. m.OlG]. Ventral Surface: Moderate yellow green [120. m.YG].

*Red midvein.*—Absent.

*Margin.*—Finely serrate.

*Venation.*—Pinnately net veined.

*Vein color.*—Light yellow green [119. l.YG].

*Petiole.*—Average Length: ½" [12.7 mm.]. Average Thickness: 1/16" [1.6 mm.]. Color: Brilliant yellow green [116. brill.YG].

*Stipules.*—Number: Typically two per leaf, up to six per growing tip. Average Length: 5/16" [7.9 mm.]. Color: Very yellow green [115. v.YG] becoming Dark yellowish brown [78. d.yBr] with maturity.

*Glands.*—Number: 2 to 6 per leaf. Position: Mostly alternate, on the petiole and base of blade. Form: Reniform. Size: Medium, about 1/24" [1.1 mm.] in length, about 1/48" [0.5 mm.] in width.

*Leaf buds.*—Pointed.

Flower buds:

*Hardiness.*—Hardy, with respect to central California blooming season.

*Diameter.*—Typically ⅜" [9.5 mm.] 1 week before bloom.

*Length.*—Typically ⅝" [15.9 mm.] 1 week before bloom.

*Form.*—Not appressed.

*Surface.*—Pubescent.
*Tip color.*—Light pink [4. l.Pk].

Flowers: Perfect, complete, perigynous, usually a single pistil, about thirty stamens, five sepal and petal locations alternately positioned.
*Type.*—Showy, medium to large.
*Average flower diameter.*—1 13/16" [46.0 mm.].
*Average flower depth.*—7/16" [11.1 mm.] when fully open.
*Number of petals.*—Five, extra petal fragments rarely observed, double blossoms not observed.
*Petal shape.*—Circular to oval.
*Petal margin.*—Entire, slightly wavy.
*Average petal diameter.*—¾" [19.1 mm.].
*Average petal length.*—¾" [19.1 mm.].
*Petal apex.*—Rounded.
*Petal base.*—Rounded.
*Petal color.*—Pale pink [7. p.Pk] toward the apex and Light pink [4. l.Pk] toward the base on both sides.
*Anthocyanin coloration intensity.*—Weak.
*Anther color.*—Moderate reddish orange [37. m.rO] over a Light yellow [86. l.Y] center at bloom onset.
*Pollen.*—Anthers produce an abundance of Brilliant yellow [83. brill.Y] pollen.
*Stigma color.*—Light greenish yellow [101. l.gY].
*Stigma position.*—Typically located slightly above the nearby anthers.
*Ovary.*—Pubescent.
*Sepal color.*—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length.*—¼" [6.4 mm.].
*Sepal width.*—7/32" [5.6 mm.].
*Sepal apex.*—Rounded to elliptical to match the sepal length and width.
*Sepal margin.*—Fairly smooth.
*Sepal outer surface.*—Pubescent.
*Average pistil length.*—⅝" [15.9 mm.].
*Average stamen length.*—7/16" [11.1 mm.].
*Fragrance.*—Moderate.
*Blooming period.*—Early, blooms seven days before 'Pearl Princess V' (U.S. Plant Pat. No. 19,919) peach.
*Onset of bloom.*—One percent on Feb. 7, 2015.
*Date of full bloom.*—Feb. 17, 2015.
*Duration of bloom.*—One to two weeks, dependent on ambient temperature.
*Bloom density.*—Medium to heavy.
*Number per cluster.*—1 to 3 with single flowers most common.

FRUIT

Maturity when described: Shipping ripe, Jun. 5, 2015.
Date of first picking: Jun. 3, 2015.
Date of last picking: Jun. 12, 2015.
Size: Uniform, large.
*Average diameter axially.*—3⅛" [79.4 mm.].
*Average diameter across suture plane.*—3⅛" [79.4 mm.].
*Average diameter across cheek plane.*—3⅛" [79.4 mm.].
*Typical weight.*—10.4 ounces [295 grams].
Form: Uniform, globose, symmetrical.
*Longitudinal section form.*—Round.
*Axial view.*—Round.
Suture: A shallow groove extending from the base to beyond the pistil point.
*Near the base.*—A sharp groove.
*Along the side.*—A shallow groove.
*Near the apex.*—A shallow groove.
Ventral surface: Rounded to slightly protruding.
Lips: Lipped slightly toward the apex on both sides. Lips are slightly unequal.
Cavity: Flaring, elongated in the suture plane, suture showing on one side, Pale greenish yellow [104. p.gY] stem markings typical.
*Depth.*—⅝" [15.9 mm.].
*Breadth.*—1 3/16" [30.2 mm.].
Base: Rounded to somewhat truncate and slightly cordate if viewed parallel to the suture.
Apex: Rounded with slight mammification on about forty percent.
Pistil point: Apical, very short with a typical length of 1/32" [0.8 mm.].
Stem: Medium.
*Average length.*—⅜" [9.5 mm.].
*Average width.*—3/16" [4.8 mm.].
Skin:
*Thickness.*—Medium.
*Surface.*—Pubescent.
*Density of the pubescence.*—Medium.
*Down.*—Short, does not roll up when rubbed.
*Tenacity.*—Tenacious to flesh.
*Astringency.*—Very slight.
*Tendency to crack.*—None observed.
*Color.*—Very dark red [17. v.d.R] blending into a Strong pink [2. s.Pk] background with a minor amount of Pale yellowish pink [31. p.yPk] freckling toward the apex.
Flesh:
*Color.*—Greenish white [153. gWhite] with very slight Moderate pink [5. m.Pk] bleeding very close to the stone.
*Surface of pit cavity.*—Covered with Pale greenish yellow [104. p.gY] and Moderate pink [5. m.Pk] broken fibers when twisted away from the stone.
*Amygdalin.*—Scant.
*Juice.*—Moderate.
*Texture.*—Firm, crisp, melting.
*Fibers.*—Few, fine.
*Ripens.*—Fairly even, slightly earlier toward the apex.
*Flavor.*—Sub-acid, mild, somewhat sweet, typically 14 brix.
*Aroma.*—Very slight.
*Eating quality.*—Good.

STONE

Type: Clingstone.
Form: Elliptical.
Hilum: Narrow.
Base: Rounded.
Apex: Acuminate.
Sides: Equal.
Tip: ⅛" [3.2 mm.], sharp angle.
Surface: Irregularly furrowed near the apex, pitted toward the base.

Ridges: Jagged.
External color: Pale orange yellow [73. p.OY].
Pit wall color when cracked: Pale orange yellow [73. p.OY].
Cavity surface color: A two-tone of Strong yellowish brown [74. s.yBr] and Light yellowish brown [76. l.yBr].
Average pit wall thickness: ¼" [6.4 mm.].
Average length: 1 11/16" [42.9 mm.].
Average width: 1" [25.4 mm.].
Average breadth: 13/16" [20.6 mm.].
Tendency to split: None observed.
Kernel:

*Form.*—Oval.
*Skin color.*—Light yellow [86. l.Y] when first removed.
*Pellicle color.*—Grayish yellow [90. gy.Y].
*Vein color.*—Brilliant yellow [83. brill.Y] when first removed becoming Deep orange yellow [69. deep OY] after thirty minutes of exposure.
*Taste.*—Bitter.
*Viable.*—Yes.
*Average length.*—13/16" [20.6 mm.].
*Average width.*—½" [12.7 mm.].
*Amygdalin.*—Moderate.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to its seed parent, 'Pearl Princess V' (U.S. Plant Pat. No. 19,919) peach, by having showy blossoms, by having reniform leaf glands, by being self-fertile, and by producing white flesh peaches that are mostly red in skin color, nearly globose in shape, and firm in texture, but is distinguished therefrom by having a smaller and less vigorous tree, by blooming earlier, by requiring less chilling hours, and by producing fruit that is clingstone instead of freestone in type, that is somewhat lower in acid, and that matures about seven days earlier.

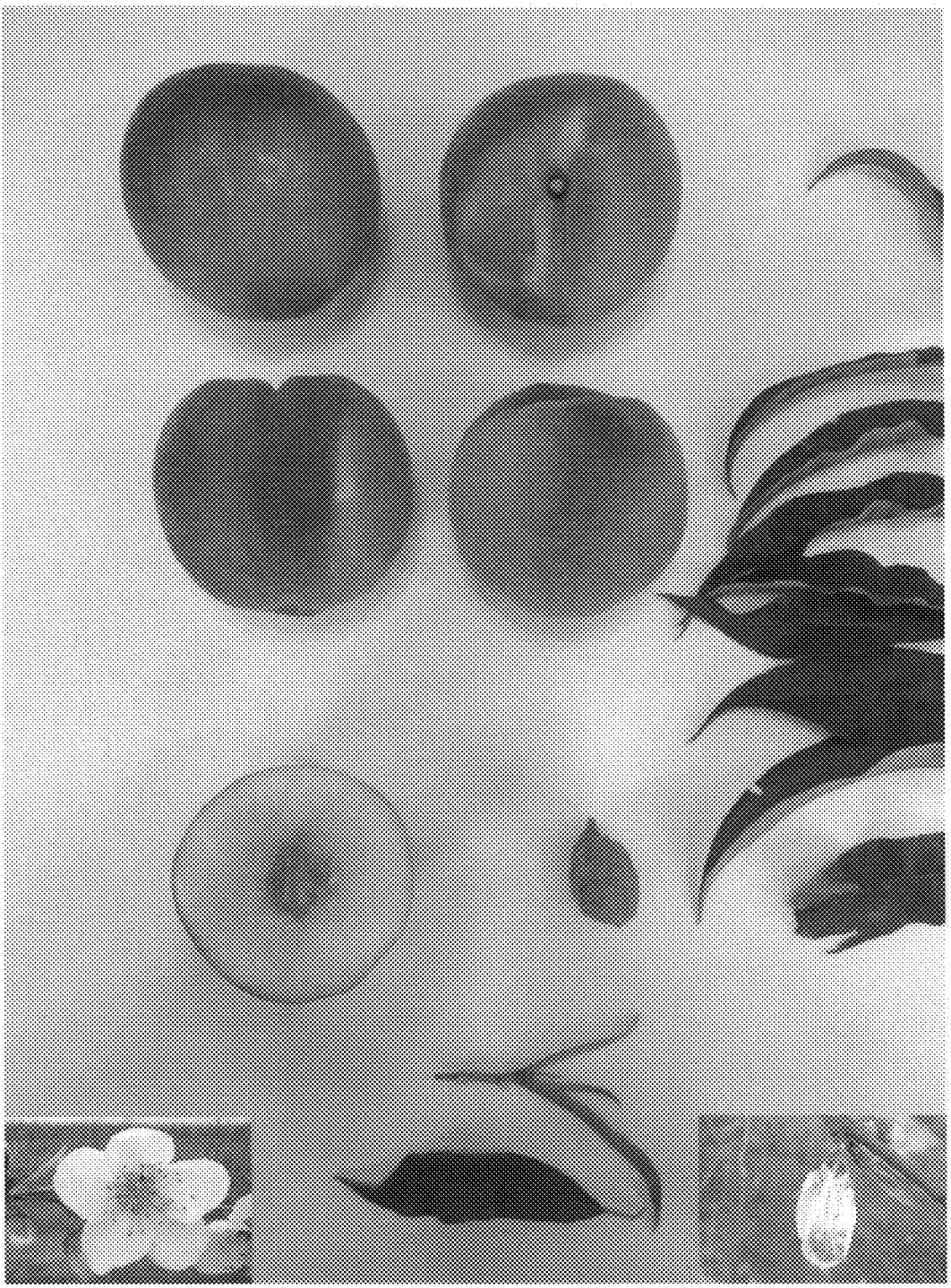

* * * * *